(12) United States Patent
Takeda et al.

(10) Patent No.: US 11,305,034 B2
(45) Date of Patent: Apr. 19, 2022

(54) STRETCHABLE FILM AND PRODUCT INCLUDING SAME

(71) Applicant: NITTO DENKO CORPORATION, Osaka (JP)

(72) Inventors: Kohei Takeda, Ibaraki (JP); Shou Uchida, Ibaraki (JP); Muneshige Nakagawa, Ibaraki (JP); Shinsuke Ikishima, Ibaraki (JP); Yasuhiro Takeda, Matsuyama (JP); Yoshitake Shigematsu, Matsuyama (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/564,302

(22) PCT Filed: Apr. 12, 2016

(86) PCT No.: PCT/JP2016/061788
§ 371 (c)(1),
(2) Date: Oct. 4, 2017

(87) PCT Pub. No.: WO2016/167242
PCT Pub. Date: Oct. 20, 2016

(65) Prior Publication Data
US 2018/0133357 A1     May 17, 2018

(30) Foreign Application Priority Data

Apr. 15, 2015 (JP) .............................. JP2015-082962
Mar. 22, 2016 (JP) .............................. JP2016-056671

(51) Int. Cl.
*A61L 15/24* (2006.01)
*A61L 15/18* (2006.01)
(Continued)

(52) U.S. Cl.
CPC ........ *A61L 15/24* (2013.01); *A61F 13/00012* (2013.01); *A61F 13/15203* (2013.01);
(Continued)

(58) Field of Classification Search
CPC ....... B29D 7/01; B32B 27/205; B32B 27/327; C08J 9/00
See application file for complete search history.

(56) References Cited

U.S. PATENT DOCUMENTS 4,335,225 A * 6/1982 Collette ................ C08F 110/06
525/240
4,472,328 A 9/1984 Sugimoto et al.
(Continued)

FOREIGN PATENT DOCUMENTS

CN     1312319     9/2001
CN     1839042     9/2006
(Continued)

OTHER PUBLICATIONS

Ueda—JP H07-286051 A—MT—Expansible sheet—ISR D6—1995 (Year: 1995).*
(Continued)

*Primary Examiner* — Callie E Shosho
*Assistant Examiner* — John Vincent Lawler
(74) *Attorney, Agent, or Firm* — Greenblum & Bernstein, P.L.C.

(57) ABSTRACT

Provided is a stretchable film having excellent stretchability and excellent air permeability. Also provided is an article including such stretchable film. The stretchable film of the present invention includes an olefin-based resin and a filler.

15 Claims, 2 Drawing Sheets

(51) Int. Cl.

| | | |
|---|---|---|
| C08J 9/00 | (2006.01) | |
| C08K 3/26 | (2006.01) | |
| C08L 23/04 | (2006.01) | |
| B32B 27/32 | (2006.01) | |
| A61F 13/00 | (2006.01) | |
| B29C 55/00 | (2006.01) | |
| A61F 13/514 | (2006.01) | |
| B29C 55/04 | (2006.01) | |
| A61F 13/511 | (2006.01) | |
| C08J 5/18 | (2006.01) | |
| A61L 15/20 | (2006.01) | |
| A61L 15/42 | (2006.01) | |
| C08L 23/14 | (2006.01) | |
| B32B 27/08 | (2006.01) | |
| B32B 27/30 | (2006.01) | |
| B32B 27/20 | (2006.01) | |
| B32B 27/36 | (2006.01) | |
| B32B 3/26 | (2006.01) | |
| B29D 7/01 | (2006.01) | |
| C08K 13/04 | (2006.01) | |
| B29C 55/10 | (2006.01) | |
| A61F 13/15 | (2006.01) | |
| A61F 13/49 | (2006.01) | |
| A61L 15/22 | (2006.01) | |
| C08L 23/12 | (2006.01) | |
| B29K 23/00 | (2006.01) | |
| B29L 31/48 | (2006.01) | |
| B29K 105/16 | (2006.01) | |

(52) U.S. Cl.
CPC .. *A61F 13/49009* (2013.01); *A61F 13/51121* (2013.01); *A61F 13/51401* (2013.01); *A61L 15/18* (2013.01); *A61L 15/20* (2013.01); *A61L 15/225* (2013.01); *A61L 15/42* (2013.01); *B29C 55/005* (2013.01); *B29C 55/04* (2013.01); *B29C 55/10* (2013.01); *B29D 7/01* (2013.01); *B32B 3/266* (2013.01); *B32B 27/08* (2013.01); *B32B 27/20* (2013.01); *B32B 27/205* (2013.01); *B32B 27/306* (2013.01); *B32B 27/308* (2013.01); *B32B 27/32* (2013.01); *B32B 27/327* (2013.01); *B32B 27/36* (2013.01); *C08J 5/18* (2013.01); *C08J 9/00* (2013.01); *C08K 3/26* (2013.01); *C08K 13/04* (2013.01); *C08L 23/04* (2013.01); *C08L 23/12* (2013.01); *C08L 23/14* (2013.01); *A61F 2013/15552* (2013.01); *B29K 2023/00* (2013.01); *B29K 2105/16* (2013.01); *B29K 2995/0065* (2013.01); *B29L 2031/4835* (2013.01); *B29L 2031/4878* (2013.01); *B32B 2250/03* (2013.01); *B32B 2250/40* (2013.01); *B32B 2264/025* (2013.01); *B32B 2264/0235* (2013.01); *B32B 2264/102* (2013.01); *B32B 2264/104* (2013.01); *B32B 2270/00* (2013.01); *B32B 2307/50* (2013.01); *B32B 2307/724* (2013.01); *B32B 2555/02* (2013.01); *C08J 2323/12* (2013.01); *C08J 2423/16* (2013.01); *C08K 2003/265* (2013.01); *C08K 2201/003* (2013.01); *C08K 2201/005* (2013.01); *C08L 2203/02* (2013.01); *C08L 2203/16* (2013.01); *C08L 2205/025* (2013.01)

(56) References Cited

U.S. PATENT DOCUMENTS

| | | | |
|---|---|---|---|
| 4,613,643 A * | 9/1986 | Nakamura | C08L 23/0815 524/426 |
| 4,921,652 A | 5/1990 | Tsuji et al. | |
| 5,001,205 A * | 3/1991 | Hoel | C08F 210/16 502/117 |
| 5,185,035 A | 2/1993 | Krueger et al. | |
| 5,366,782 A | 11/1994 | Curro et al. | |
| 5,385,972 A | 1/1995 | Yamamoto et al. | |
| 5,501,679 A | 3/1996 | Krueger et al. | |
| 5,691,034 A | 11/1997 | Krueger et al. | |
| 5,968,643 A * | 10/1999 | Topolkaraev | C08J 9/18 428/305.5 |
| 6,120,487 A | 9/2000 | Ashton | |
| 6,169,151 B1 | 1/2001 | Waymouth et al. | |
| 6,322,883 B1 * | 11/2001 | Williams | B29C 55/023 428/308.4 |
| 6,472,445 B1 | 10/2002 | Takahashi et al. | |
| 6,514,606 B2 | 2/2003 | Kinoshita et al. | |
| 6,518,378 B2 | 2/2003 | Waymouth et al. | |
| 6,555,643 B1 | 4/2003 | Rieger | |
| 6,559,262 B1 | 5/2003 | Waymouth et al. | |
| 6,703,439 B2 | 3/2004 | Yano et al. | |
| 7,220,478 B2 * | 5/2007 | McCormack | B29C 47/0004 428/304.4 |
| 7,270,723 B2 | 9/2007 | McCormack et al. | |
| 7,279,723 B2 | 10/2007 | McCormack et al. | |
| 8,235,963 B2 | 8/2012 | Lodge et al. | |
| 8,343,126 B2 | 1/2013 | Lodge et al. | |
| 8,777,917 B2 | 7/2014 | Lodge et al. | |
| 9,072,633 B2 | 7/2015 | Autran et al. | |
| 2001/0018465 A1 | 8/2001 | Yano et al. | |
| 2002/0064651 A1 | 5/2002 | Kinoshita et al. | |
| 2004/0170852 A1 | 9/2004 | Gustafson | |
| 2005/0043460 A1 | 2/2005 | McCormack et al. | |
| 2005/0101206 A1 | 5/2005 | McCormack et al. | |
| 2006/0024520 A1 * | 2/2006 | Kong | B32B 3/26 428/517 |
| 2007/0287348 A1 | 12/2007 | Autran et al. | |
| 2007/0287982 A1 | 12/2007 | Lodge et al. | |
| 2007/0287983 A1 | 12/2007 | Lodge et al. | |
| 2008/0004582 A1 | 1/2008 | Lodge et al. | |
| 2008/0004583 A1 | 1/2008 | Desai et al. | |
| 2008/0004584 A1 | 1/2008 | Langdon et al. | |
| 2008/0004586 A1 | 1/2008 | Lodge et al. | |
| 2008/0004587 A1 | 1/2008 | Lodge et al. | |
| 2008/0004589 A1 | 1/2008 | Roe et al. | |
| 2008/0004590 A1 | 1/2008 | Lodge et al. | |
| 2008/0004591 A1 | 1/2008 | Desai et al. | |
| 2008/0004592 A1 | 1/2008 | Lodge et al. | |
| 2008/0004593 A1 | 1/2008 | Lodge et al. | |
| 2008/0015537 A1 | 1/2008 | Lodge et al. | |
| 2008/0045917 A1 * | 2/2008 | Autran | A61F 13/51464 604/385.22 |
| 2008/0125739 A1 | 5/2008 | Lodge et al. | |
| 2008/0188822 A1 | 8/2008 | Lodge et al. | |
| 2009/0258210 A1 * | 10/2009 | Iyad | B32B 25/08 428/220 |
| 2016/0159031 A1 | 6/2016 | Ikishima et al. | |
| 2016/0200078 A1 | 7/2016 | Arakawa | |
| 2018/0133951 A1 | 5/2018 | Takeda | |

FOREIGN PATENT DOCUMENTS

| | | | |
|---|---|---|---|
| EP | 0993832 | 4/2000 | |
| EP | 1256594 | 11/2002 | |
| EP | 1250225 | 8/2005 | |
| EP | 1656246 | 5/2006 | |
| EP | 1864793 A1 * | 12/2007 | ............ C09J 123/14 |
| EP | 3023247 A1 | 5/2016 | |
| EP | 3045311 A1 | 7/2016 | |
| JP | S58-15538 | 1/1983 | |
| JP | S60-166436 | 8/1985 | |
| JP | S62-148537 | 7/1987 | |
| JP | H05-18856 B | 3/1993 | |

(56) References Cited

FOREIGN PATENT DOCUMENTS

| | | | |
|---|---|---|---|
| JP | H05-050522 | 3/1993 | |
| JP | H05-501386 A | 3/1993 | |
| JP | 5-310980 | 11/1993 | |
| JP | H07-286051 A | 10/1995 | |
| JP | H07286051 * | 10/1995 | ............ A41D 27/10 |
| JP | H08-053561 | 2/1996 | |
| JP | H10-139953 | 5/1998 | |
| JP | H10-139953 A | 5/1998 | |
| JP | H11-048410 | 2/1999 | |
| JP | H11-048410 A | 2/1999 | |
| JP | H11-151782 | 6/1999 | |
| JP | H11-151782 A | 6/1999 | |
| JP | H11151782 * | 6/1999 | ............ B32B 25/08 |
| JP | H11-240984 | 9/1999 | |
| JP | H11-245338 A | 9/1999 | |
| JP | H11-291404 A | 10/1999 | |
| JP | 2000-001557 A | 1/2000 | |
| JP | 2000-167037 | 6/2000 | |
| JP | 2002-146070 | 5/2002 | |
| JP | 3308025 | 5/2002 | |
| JP | 2002-307627 A | 10/2002 | |
| JP | 2002-316359 | 10/2002 | |
| JP | 2008-169304 A | 7/2006 | |
| JP | 2008-088293 | 4/2008 | |
| JP | 2008169304 * | 7/2008 | ............... C08K 3/26 |
| JP | 2008-179757 | 8/2008 | |
| JP | 2009-114434 A | 5/2009 | |
| JP | 2009-126000 A | 6/2009 | |
| JP | 2009-539481 A | 11/2009 | |
| JP | 2010-065088 | 3/2010 | |
| JP | 2012-177106 | 9/2012 | |
| JP | 2013-040261 A | 2/2013 | |
| JP | 2015-20317 | 2/2015 | |
| JP | 2015-021105 A | 2/2015 | |
| JP | 2015-063633 | 4/2015 | |
| JP | 2015-063633 A | 4/2015 | |
| JP | 2015-86367 A | 5/2015 | |
| WO | 01/47710 | 7/2001 | |
| WO | 01/47710 A1 | 7/2001 | |
| WO | 2005/023544 | 3/2005 | |
| WO | 2015/008595 | 1/2015 | |
| WO | 2015/037507 | 3/2015 | |
| WO | 2016/167241 | 10/2016 | |

OTHER PUBLICATIONS

Toda—JP H11-151782 A—MT—stretchable composite film—ISR D1—1999 (Year: 1999).*
Toda—JP 2008-169304 A—MT—resin for stretch film—2008 (Year: 2008).*
Series_TAFMER™, a high performance elastomer—Mitsui Chemicals (Year: 2018).*
Ueda—JP H07-286051 A—Expansible sheet—ISR D6—1995—Human translation (Year: 1995).*
Collette—elastomeric polypropylenes—Macro—1989 (Year: 1989).*
Vistamaxx 6202 datasheet—2017 (Year: 2017).*
ExxonMobil—Vistamaxx 6102 datasheet—B—Jan. 2017 (Year: 2017).*
Mitsui Chemicals—TAFMER A grades_a—2011 (Year: 2011).*
Zanchin—Polyolefin thermoplastic elastomers—Vistamaxx e-pp copolymer—Prog.Poly.Sci.—2021 (Year: 2021).*
ChemEurope.com—Polypropylene—Oct. 12, 2021 (Year: 2021).*
International Search Report from Application No. PCT/JP2016/061788, dated Jun. 21, 2016.
International Preliminary Report on Patentability from Application No. PCT/JP2016/061788, dated Oct. 17, 2017.
Supplementary European Search Report dated Jan. 28, 2019 in European Application No. 16780033.
Third Party Observation dated Jul. 30, 2019 filed in Japanese patent application No. 2015-232629, with English translation.
The Micropedia of the Britannica International Encyclopedia, "permanent set", downloaded Jul. 10, 2019, https://kotobank.jp/word/% E%BC%B0%B8%E4B9%85%E3%81%B2%E3%81%9A%E3% 81%BF-35835 with English translation.
The Micropedia of the Britannica International Encyclopedia, "elongation percentage", downloaded Jul. 10, 2019, https://kotobank.jp/ word/%E6%B0%B8%E4%B95581%B3%E7%8E%87-112372) with English translation.
"Basic Physical Properties of Tafmer DF & A Brands", download undated, https://www.mitsuichem.com/sites/default/files/media/ document/2018/brand001_2.pdf with English Translation.
Elastomers Division, Mobility Business Sector, Mitsui Chemicals, Inc., "Product Introduction of Tafmer", download undated (indicates Aug. 24, 2018 document), https://www.chem-t.com/fax/images/ tmp_file4_1535093776.pdf) with English translation.
Plastics Today, "Exxon's Singapore expansion on schedule; Vistamaxx broadened", downloaded Jul. 11, 2019 (indicates Apr. 27, 2010 document), https://www.plasticstoday.com/content/exxon-s-singapore-expansion-on-schedule-vistamaxx-broadened/10727890114121.
ExxonMobil Japan G.K., "Propylene-based Elastomer "Vistamaxx Series, downloaded Jul. 11, 2019, https://www.ipros.jp/product/ detail/print/?objectId=1504356&hub=45+goggle with English translation.
Junichi Imuta, "Synthesis of Elastomers by Metallocene Catalysts", download undated, https://www.jstage.jst.go.ip/article/kobunshi1952/ 46/11/46_11_824/_pdf with English translation.
Glossary of Technical Terms in Manufacturing Industry, "Melt Flow Rate", downloaded Jul. 22, 2019,https://www.ipros.jp/monosiri/ term/%E3%83%A1%E3%83%AB%E3%83%88%E3%83%95%E3% 83%AD%E3%83%BC%E3%83%AC%E3%83%BC%E3%83%88 with English translation.
International Search Report from Application No. PCT/JP2016/ 061787, dated Jul. 19, 2016, with English Translation.
International Preliminary Report on Patentability from Application No. PCT/JP2016/061787, dated Oct. 17, 2017, with English translation.
Supplementary European Search Report issued on Jul. 28, 2019 in European Application No. 16780033.
Buschow, K. H. J. (2001). Encyclopedia of materials: Science and technology. Amsterdam: Elsevier. p. 7705-7708 (Year: 2001).
Office Action dated Oct. 9, 2019 in U.S. Appl. No. 15/564,090.
Office Action issued in Japanese Patent Application No. 2016-056671, dated Sep. 24, 2019, with English translation.
Office Action issued in JP Patent Application No. 2015-232629, dated Sep. 24, 2019, with English translation.
Office Action dated Mar. 30, 2020 in European Application No. 16780033.3.
Mar. 2, 2020 Office Action in commonly assigned copending U.S. Appl. No. 15/564,090.
Office Action dated Dec. 10, 2019 in Chinese Application No. 201680021971.1 with English translation.
Office Action dated Nov. 20, 2019 in Chinese Application No. 201680021935.5 with English translation.
Office Action dated May 26, 2020 in Japanese Application No. 2016-056671 with English translation.
Yutaka Kikuchi et al., Structure and Properties of Thermoplastic Elastomer, Journal of the Society of Rubber Science and Technology, Japan, 1991, vol. 64, No. 9, pp. 38-44, "Development and Perspective of Elastomer Engineering" with English translation.
Written Patent Opposition dated Jan. 18, 2021 to the corresponding Japanese patent No. 6726953 (JP appln 2015-232629) which was mailed on Feb. 15, 2021 with English translation thereof, citing Document "a" as Exhibit No. 2.
The written argument regarding JP2015-232629 dated Nov. 21, 2019 with English translation thereof, cited in Document 1, as Exhibit No. 7.
Koji Takahashi, "ISO Pulp and Paper Test Standard Proposed for the First Time by Japan: Determination of Air Permeance/Oken Method," Journal of Printing Science and Technology, vol. 52, issue 3, pp. 245-249 (2015) with English translation thereof, cited in Document 1, as Exhibit 9.
Notice of Reasons for Revocation dated May 26, 2021, issued in corresponding Japanese Patent Opposition No. 2021-700235 (JP (56) References Cited

OTHER PUBLICATIONS

Patent No. 6751573, JP appln. 2016056671)) with English machine translation thereof, citing Documents A, B, C, D, and "a" on p. 8 of the English translation.

Written Patent Opposition dated Mar. 1, 2021 to the corresponding Japanese patent No. 6751573 (JP appln 2016056671) which was mailed on Apr. 1, 2021 with English translation thereof, citing Document "A" on p. 10 of English translation.

The written argument regarding JP2016-056671 dated Jul. 21, 2020 with English translation thereof, cited in Document 1, as Exhibit No. 4.

Vistamaxx™ Catalog (2014), with English translation thereof, cited in Document 1, as Exhibit No. 3.

TAFMER®PN. https://jp.mitsuichemicals.com/jp/service/mobility/mels/tafmer-pn/index.htm, with English translation thereof, cited in Document 1, as Exhibit No. 6.

Notice of Reasons for Revocation dated Sep. 17, 2021, issued in corresponding Japanese patent opposition No. 2021-700057 (patent No. 6726953, JP appln. 2015-232629) with English machine translation thereof, citing document A at p. 11 of the English translation.

Opponent's Written Opinion dated Jul. 16, 2021 to the corresponding Japanese patent opposition No. 2021-700057 (patent No. 6726953, JP appln. 2015-232629) with English translation thereof, citing document "a" at p. 8 of the English translation.

\* cited by examiner

STRETCHABLE FILM AND PRODUCT INCLUDING SAME

TECHNICAL FIELD

The present invention relates to a stretchable film and an article including the stretchable film.

BACKGROUND ART

Various stretchable films are adopted for articles such as sanitary articles, for example, a diaper and a mask (for example, Patent Literature 1).

Such stretchable film is required to have not only excellent stretchability but also excellent air permeability in view of applications such as a diaper and a mask.

CITATION LIST

Patent Literature

[PTL 1] JP 05-501386 A

SUMMARY OF INVENTION

Technical Problem

The present invention has been made to solve the conventional problems, and an object of the present invention is to provide a stretchable film having excellent stretchability and excellent air permeability. Another object of the present invention is to provide an article including such stretchable film.

Solution to Problem

A stretchable film according to one embodiment of the present invention includes: an olefin-based resin; and a filler.

In a preferred embodiment, the olefin-based resin contains an olefin-based elastomer.

In a preferred embodiment, the olefin-based resin contains an α-olefin-based elastomer.

In a preferred embodiment, the α-olefin-based elastomer includes at least one kind selected from an ethylene-based elastomer and a propylene-based elastomer.

In a preferred embodiment, the α-olefin-based elastomer is produced by using a metallocene catalyst.

In a preferred embodiment, the filler includes at least one kind selected from inorganic particles and organic particles.

In a preferred embodiment, the filler has an average particle diameter of from 0.5 μm to 50 μm.

In a preferred embodiment, the filler has an average particle diameter of from 0.7 μm to 5 μm.

In a preferred embodiment, a content of the filler is from 50 parts by weight to 400 parts by weight with respect to 100 parts by weight of the olefin-based resin.

In a preferred embodiment, the content of the filler is from 100 parts by weight to 300 parts by weight with respect to 100 parts by weight of the olefin-based resin.

In a preferred embodiment, the stretchable film according to the embodiment of the present invention is formed of a laminate of two or more layers.

In a preferred embodiment, the stretchable film according to the embodiment of the present invention is formed of a laminate of three layers, the laminate having a layer construction "A layer/B layer/C layer."

In a preferred embodiment, the B layer contains an olefin-based elastomer and is free of a non-elastomeric olefin-based resin.

In a preferred embodiment, the layer construction includes one of (1) a construction "[layer containing a non-elastomeric olefin-based resin as a resin component]/[layer containing an olefin-based elastomer as a resin component]/[layer containing the non-elastomeric olefin-based resin as a resin component]," and (2) a construction "[layer containing a blend of an olefin-based elastomer and a non-elastomeric olefin-based resin as a resin component]/[layer containing the olefin-based elastomer as a resin component]/[layer containing the blend of the olefin-based elastomer and the non-elastomeric olefin-based resin as a resin component]."

In a preferred embodiment, the stretchable film according to the embodiment of the present invention is obtained by subjecting an unstretched film to a stretching treatment.

In a preferred embodiment, the stretchable film according to the embodiment of the present invention has voids in a surface thereof.

In a preferred embodiment, stretching of the stretchable film according to the embodiment of the present invention produces voids in a surface thereof.

In a preferred embodiment, the stretchable film according to the embodiment of the present invention is used in a sanitary article.

An article according to one embodiment of the present invention includes the stretchable film according to the embodiment of the present invention.

Advantageous Effects of Invention

According to the present invention, the stretchable film having excellent stretchability and excellent air permeability can be provided. The article including such stretchable film can also be provided.

DESCRIPTION OF EMBODIMENTS

«Stretchable Film»

A stretchable film of the present invention includes an olefin-based resin and a filler.

The stretchable film of the present invention may be formed only of one layer, or may be formed of a laminate of two or more layers.

Any appropriate thickness may be adopted as the thickness of the stretchable film of the present invention to the extent that the effects of the present invention are not impaired. Such thickness is preferably from 20 μm to 150 μm, more preferably from 40 μm to 150 μm.

Figure 1:
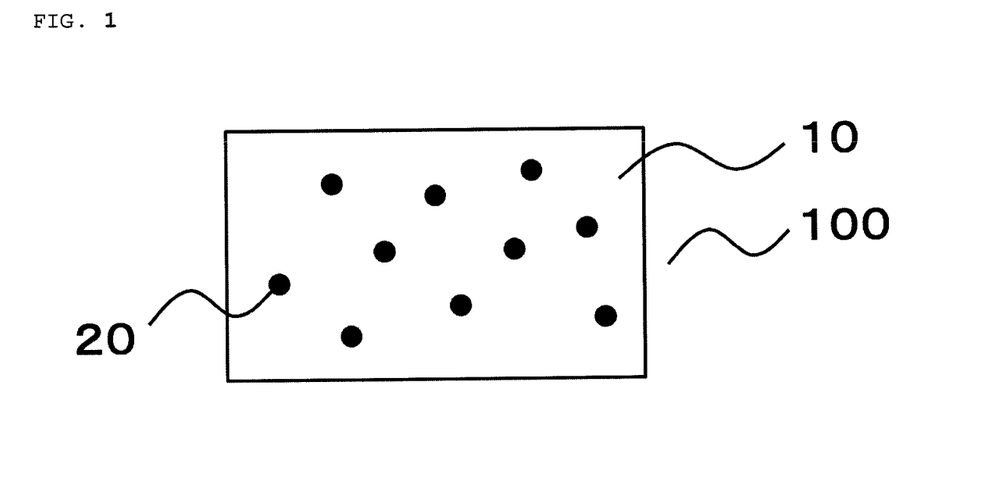
FIG. 1 is a schematic plan view of an example of a stretchable film according to a preferred embodiment of the present invention.

FIG. 1 is a schematic plan view of an example of a stretchable film according to a preferred embodiment of the present invention. In FIG. 1, a stretchable film 100 includes an olefin-based resin 10 and a filler 20.

Figure 2:
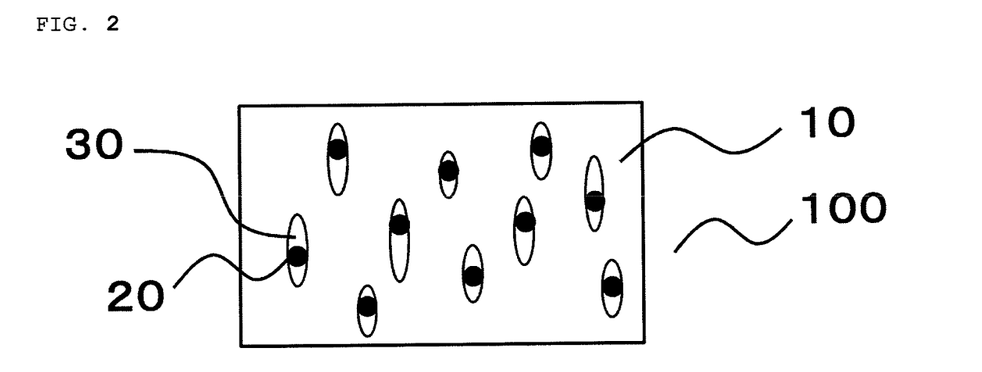
FIG. 2 is a schematic plan view of another example of the stretchable film according to the preferred embodiment of the present invention.

FIG. 2 is a schematic plan view of another example of the stretchable film according to the preferred embodiment of the present invention. In FIG. 2, a stretchable film 100 includes an olefin-based resin 10 and a filler 20 and further includes voids 30.

When the stretchable film of the present invention is such embodiment as illustrated in FIG. 1, the stretchable film may be turned into such embodiment as illustrated in FIG. 2 by being stretched. That is, when the stretchable film of the present invention is such embodiment as illustrated in FIG. 1, the stretching of the stretchable film of the present invention may produce voids in its surface.

In the case where the stretchable film of the present invention is such embodiment as illustrated in FIG. 1, the stretchable film can express excellent air permeability even when not stretched. In addition, in the case where the stretchable film of the present invention is such embodiment as illustrated in FIG. 1, the stretchable film can express excellent air permeability by being stretched.

In the case where the stretchable film of the present invention is such embodiment as illustrated in FIG. 2, the stretchable film can express excellent air permeability even when not stretched. In addition, in the case where the stretchable film of the present invention is such embodiment as illustrated in FIG. 2, the stretchable film can express more excellent air permeability by being stretched.

Such embodiment as illustrated in FIG. 1 or such embodiment as illustrated in FIG. 2 may be adopted as the stretchable film of the present invention in accordance with performance required of a site to be used in an application such as a diaper or a mask. For example, when the stretchable film of the present invention is such embodiment as illustrated in FIG. 1, the embodiment being capable of expressing excellent air permeability even when not stretched, the stretchable film can be preferably used in a site where expansion and contraction hardly occur, the site being required to have air permeability. In addition, for example, when the stretchable film of the present invention is such embodiment as illustrated in FIG. 1, the embodiment being capable of expressing excellent air permeability by being stretched, the stretchable film can be preferably used in a site where expansion and contraction occur, the site being required to have air permeability. Further, when the stretchable film of the present invention is such embodiment as illustrated in FIG. 2, the stretchable film can be preferably used in a site where expansion and contraction hardly occur, the site being required to have air permeability, or in a site where expansion and contraction occur, the site being required to have air permeability.

The stretchable film of the present invention includes the olefin-based resin.

The olefin-based resin may be only one kind of resin, or may be a blend of two or more kinds of resins.

The term "olefin-based resin" as used herein is meant to include an "olefin-based elastomer" having an elastomeric property and a "non-elastomeric olefin-based resin" free of any elastomeric property. That is, when the term "olefin-based resin" is used in this description, unless particular limitative description is present, the term means that the following three cases may be present: a case in which the resin is only an "olefin-based elastomer;" a case in which the resin is only a "non-elastomeric olefin-based resin;" and a case in which the resin is a blend of an "olefin-based elastomer" and a "non-elastomeric olefin-based resin."

The olefin-based resin preferably contains an olefin-based elastomer. When the olefin-based resin contains the olefin-based elastomer, the stretchable film of the present invention can express excellent stretchability. In addition, when the olefin-based resin contains the olefin-based elastomer, the stretchable film of the present invention can express excellent air permeability by being combined with the filler. In addition, when the olefin-based resin contains the olefin-based elastomer, an odor generated from the stretchable film of the present invention can be suppressed.

The olefin-based elastomer may be only one kind of elastomer, or may be a blend of two or more kinds of elastomers.

When the stretchable film of the present invention contains the olefin-based elastomer, its heat stability is improved, and hence, for example, heat decomposition at the time of the production of the stretchable film of the present invention can be suppressed. In addition, when the stretchable film of the present invention contains the olefin-based elastomer, its storage stability is improved, and hence fluctuations in physical property values during the storage of the stretchable film of the present invention can be suppressed.

In addition, when the stretchable film of the present invention contains the olefin-based elastomer, a process in the production of an elastomer layer can be simplified, and hence a processing cost can be suppressed. This is because of the following reason: when the olefin-based elastomer is adopted, resins to be used in the production of the elastomer layer can be subjected to extrusion molding while the number of kinds thereof is reduced, and hence the need for the production of a master batch can be eliminated.

When the stretchable film of the present invention is formed only of one layer, the content of the olefin-based elastomer in the olefin-based resin is preferably from 50 wt % to 100 wt %, more preferably from 70 wt % to 100 wt %, still more preferably from 90 wt % to 100 wt %, particularly preferably from 95 wt % to 100 wt %, most preferably substantially 100 wt % because the effects of the present invention are expressed to a larger extent. When the stretchable film of the present invention is formed only of one layer, the adjustment of the content of the olefin-based elastomer in the olefin-based resin within the range can make the stretchable film of the present invention excellent in oil resistance. In addition, when the stretchable film of the present invention is formed only of one layer, the adjustment of the content of the olefin-based elastomer in the olefin-based resin within the range enables the stretchable film of the present invention to express excellent stretchability. In addition, in the case where the stretchable film of the present invention is formed only of one layer, when the content of the olefin-based elastomer in the olefin-based resin is adjusted within the range, the stretchable film of the present invention can express excellent air permeability by being combined with the filler. In addition, the adjustment of the content of the olefin-based elastomer in the olefin-based resin within the range can suppress the odor generated from the stretchable film of the present invention.

When the stretchable film of the present invention is formed of a laminate of X layers, where X represents 2 or more, the stretchable film may include (X-1) or less layers each containing no olefin-based resin (other layers) to the extent that the effects of the present invention are not impaired.

When the stretchable film of the present invention is formed of a laminate of two or more layers, the number of the layers is preferably from 2 to 10, more preferably from 2 to 5, still more preferably from 2 to 4, particularly preferably 3. When the stretchable film of the present invention is formed of a laminate of three layers, the effects of the present invention can be expressed to a larger extent.

In addition, the stretchable film of the present invention can be excellent in handleability, and can be excellent in blocking resistance.

When the stretchable film of the present invention is formed of a laminate of two or more layers, all the respective layers may be of different kinds, or at least two of the layers may be of the same kind.

When the stretchable film of the present invention is formed of a laminate of two or more layers, the thickness of each layer is preferably from 2 µm to 100 µm, more preferably from 2 µm to 70 µm.

In the case where the stretchable film of the present invention is formed of a laminate of three layers, when its layer construction is represented by "A layer/B layer/C layer," the thickness of each of the A layer and the C layer serving as surface layers is preferably from 2 µm to 40 µm, more preferably from 2 µm to 30 µm, still more preferably from 2 µm to 20 µm, particularly preferably from 2 µm to 10 µm, most preferably from 2 µm to 8 µm.

In the case where the stretchable film of the present invention is formed of a laminate of three layers, when its layer construction is represented by "A layer/B layer/C layer," the thickness of the B layer serving as an intermediate layer is preferably from 10 µm to 70 µm, more preferably from 15 µm to 70 µm, still more preferably from 20 µm to 70 µm, particularly preferably from 30 µm to 70 µm, most preferably from 40 µm to 70 µm.

In the case where the stretchable film of the present invention is formed of a laminate of three layers, when its layer construction is represented by "A layer/B layer/C layer," the B layer serving as an intermediate layer may be a plurality of layers. That is, in the case of a laminate of four layers represented by "A layer/B layer/B' layer/C layer," the thickness of each layer preferably falls within the above-mentioned range while the total thickness of the B layer and the B' layer is set within the above-mentioned thickness range of the B layer.

In the case where the stretchable film of the present invention is formed of a laminate of three layers, when its layer construction is represented by "A layer/B layer/C layer," a ratio among the thicknesses of the A layer, the B layer, and the C layer is as follows: the ratio "A layer:B layer:C layer" is preferably from 1 to 30:from 40 to 98:from 1 to 30; the ratio "A layer:B layer:C layer" is more preferably from 3 to 25:from 50 to 94:from 3 to 25; the ratio "A layer:B layer:C layer" is still more preferably from 5 to 20:from 60 to 90:from 5 to 20; and the ratio "A layer:B layer:C layer" is particularly preferably from 7 to 15:from 70 to 86:from 7 to 15. When the ratio among the thicknesses of the A layer, the B layer, and the C layer falls within the range, the effects of the present invention can be expressed to a larger extent. In addition, the stretchable film of the present invention can be excellent in handleability, and can be excellent in blocking resistance.

When the stretchable film of the present invention is formed of a laminate of three layers, a form in which all of the three layers each contain an olefin-based elastomer is permitted, a form in which only two of the three layers each contain an olefin-based elastomer is also permitted, and a form in which only one of the three layers contains an olefin-based elastomer is also permitted. When the stretchable film of the present invention has such construction, the effects of the present invention can be expressed to a larger extent. In addition, the stretchable film of the present invention can be excellent in handleability, and can be excellent in blocking resistance.

When the stretchable film of the present invention is formed of a laminate of three layers, a form in which its intermediate layer (the B layer in the foregoing) contains an olefin-based elastomer and is free of a non-elastomeric olefin-based resin is more preferred. When the stretchable film of the present invention has such form, the effects of the present invention can be expressed to a larger extent. In addition, the stretchable film of the present invention can be excellent in handleability, and can be excellent in blocking resistance.

When the stretchable film of the present invention is formed of a laminate of three layers, any one of the following constructions is preferred: (1) a construction "[layer containing a non-elastomeric olefin-based resin as a resin component]/[layer containing an olefin-based elastomer as a resin component]/[layer containing the non-elastomeric olefin-based resin as a resin component];" and (2) a construction "[layer containing a blend of an olefin-based elastomer and a non-elastomeric olefin-based resin as a resin component]/[layer containing the olefin-based elastomer as a resin component]/[layer containing the blend of the olefin-based elastomer and the non-elastomeric olefin-based resin as a resin component]." When the stretchable film of the present invention has such construction, the effects of the present invention can be expressed to a larger extent. In addition, the stretchable film of the present invention can be excellent in handleability, and can be excellent in blocking resistance.

The non-elastomeric olefin-based resin may be only one kind of resin, or may be a blend or a copolymer of two or more kinds of resins.

When the stretchable film of the present invention is formed of three layers, the content of the olefin-based elastomer in the olefin-based resin is preferably from 20 wt % to 80 wt %, more preferably from 25 wt % to 75 wt %, still more preferably from 30 wt % to 70 wt %, particularly preferably from 35 wt % to 65 wt %, most preferably from 40 wt % to 60 wt % because the effects of the present invention are expressed to a larger extent. When the stretchable film of the present invention is formed of three layers, the adjustment of the content of the olefin-based elastomer in the olefin-based resin within the range can make the stretchable film of the present invention excellent in oil resistance. In addition, when the stretchable film of the present invention is formed of three layers, the adjustment of the content of the olefin-based elastomer in the olefin-based resin within the range enables the stretchable film of the present invention to express excellent stretchability. In addition, in the case where the stretchable film of the present invention is formed of three layers, when the content of the olefin-based elastomer in the olefin-based resin is adjusted within the range, the stretchable film of the present invention can express excellent air permeability by being combined with the filler. In addition, the adjustment of the content of the olefin-based elastomer in the olefin-based resin within the range can suppress the odor generated from the stretchable film of the present invention.

When the stretchable film of the present invention is formed of three layers, the content of the non-elastomeric olefin-based resin in the olefin-based resin is preferably from 20 wt % to 80 wt %, more preferably from 25 wt % to 75 wt %, still more preferably from 30 wt % to 70 wt %, particularly preferably from 35 wt % to 65 wt %, most preferably from 40 wt % to 60 wt % because the effects of the present invention are expressed to a larger extent. In the case where the stretchable film of the present invention is formed of three layers, when the content of the non-elastomeric olefin-based resin in the olefin-based resin is adjusted within the range, the effects of the present invention can be expressed to a larger extent. In addition, the stretchable film of the present invention can be excellent in handleability, and can be excellent in blocking resistance.

Examples of the olefin-based elastomer include an olefin block copolymer, an olefin random copolymer, an ethylene copolymer, a propylene copolymer, an ethylene olefin block copolymer, a propylene olefin block copolymer, an ethylene olefin random copolymer, a propylene olefin random copolymer, an ethylene propylene random copolymer, an ethylene (1-butene) random copolymer, an ethylene (1-pentene) olefin block copolymer, an ethylene (1-hexene) random copolymer, an ethylene (1-heptene) olefin block copolymer, an ethylene (1-octene) olefin block copolymer, an ethylene (1-nonene) olefin block copolymer, an ethylene (1-decene) olefin block copolymer, a propylene ethylene olefin block copolymer, an ethylene (α-olefin) copolymer, an ethylene (α-olefin) random copolymer, an ethylene (α-olefin) block copolymer, amorphous polypropylene, combinations of the above-mentioned polymers and polyethylene (LLDPE, LDPE, HDPE, or the like), combinations of the above-mentioned polymers and polypropylene, and combinations thereof.

The olefin-based elastomer has a density of preferably from $0.890$ g/cm$^3$ to $0.830$ g/cm$^3$, more preferably from $0.888$ g/cm$^3$ to $0.835$ g/cm$^3$, still more preferably from $0.886$ g/cm$^3$ to $0.835$ g/cm$^3$, particularly preferably from $0.885$ g/cm$^3$ to $0.840$ g/cm$^3$, most preferably from $0.885$ g/cm$^3$ to $0.845$ g/cm$^3$. When the olefin-based elastomer whose density falls within the range is incorporated into the elastomer layer, the stretchable film of the present invention can be even more excellent in oil resistance. In addition, the incorporation of the olefin-based elastomer whose density falls within the range into the elastomer layer enables the stretchable film of the present invention to further express excellent stretchability. In addition, when the olefin-based elastomer whose density falls within the range is incorporated into the elastomer layer, the stretchable film of the present invention can further express excellent air permeability by being combined with the filler. In addition, the incorporation of the olefin-based elastomer whose density falls within the range into the elastomer layer can further suppress the odor generated from the stretchable film of the present invention.

The olefin-based elastomer has a MFR at 230° C. and 2.16 kgf of preferably from 1.0 g/10 min to 25.0 g/10 min, more preferably from 2.0 g/10 min to 23.0 g/10 min, still more preferably from 2.0 g/10 min to 21.0 g/10 min, particularly preferably from 2.0 g/10 min to 20.0 g/10 min, most preferably from 2.0 g/10 min to 19.0 g/10 min. When the olefin-based elastomer whose MFR falls within the range is incorporated into the elastomer layer, the stretchable film of the present invention can be even more excellent in oil resistance. In addition, the incorporation of the olefin-based elastomer whose MFR falls within the range into the elastomer layer enables the stretchable film of the present invention to further express excellent stretchability. In addition, when the olefin-based elastomer whose MFR falls within the range is incorporated into the elastomer layer, the stretchable film of the present invention can further express excellent air permeability by being combined with the filler. In addition, the incorporation of the olefin-based elastomer whose MFR falls within the range into the elastomer layer can further suppress the odor generated from the stretchable film of the present invention.

The olefin-based elastomer is specifically preferably an α-olefin-based elastomer. Of such α-olefin-based elastomers, any one selected from an ethylene-based elastomer, a propylene-based elastomer, and a 1-butene-based elastomer is more preferred. When such α-olefin-based elastomer is adopted as the olefin-based elastomer, the stretchable film of the present invention can be even more excellent in oil resistance. In addition, the adoption of such α-olefin-based elastomer as the olefin-based elastomer enables the stretchable film of the present invention to further express excellent stretchability. In addition, when such α-olefin-based elastomer is adopted as the olefin-based elastomer, the stretchable film of the present invention can further express excellent air permeability by being combined with the filler. In addition, the adoption of such α-olefin-based elastomer as the olefin-based elastomer can further suppress the odor generated from the stretchable film of the present invention.

Of the α-olefin-based elastomers, an ethylene-based elastomer or a propylene-based elastomer is particularly preferred. When the ethylene-based elastomer or the propylene-based elastomer is adopted as the olefin-based elastomer, the stretchable film of the present invention can be even more excellent in oil resistance. In addition, the adoption of the ethylene-based elastomer or the propylene-based elastomer as the olefin-based elastomer enables the stretchable film of the present invention to even further express excellent stretchability. In addition, when the ethylene-based elastomer or the propylene-based elastomer is adopted as the olefin-based elastomer, the stretchable film of the present invention can even further express excellent air permeability by being combined with the filler. In addition, the adoption of the ethylene-based elastomer or the propylene-based elastomer as the olefin-based elastomer can even further suppress the odor generated from the stretchable film of the present invention.

The α-olefin-based elastomer is also available as a commercial product. Examples of such commercial product include some products in the "Tafmer" (trademark) series (e.g., Tafmer PN-2070 and Tafmer PN-3560) manufactured by Mitsui Chemicals, Inc., and some products in the "Vistamaxx" (trademark) series (e.g., Vistamaxx 6202 and Vistamaxx 7010) manufactured by Exxon Mobil Corporation.

The α-olefin-based elastomer is preferably produced by using a metallocene catalyst. When the α-olefin-based elastomer produced by using the metallocene catalyst is adopted, the stretchable film of the present invention can be even more excellent in oil resistance. In addition, the adoption of the α-olefin-based elastomer produced by using the metallocene catalyst enables the stretchable film of the present invention to even further express excellent stretchability. In addition, when the α-olefin-based elastomer produced by using the metallocene catalyst is adopted, the stretchable film of the present invention can even further express excellent air permeability by being combined with the filler. In addition, the adoption of the α-olefin-based elastomer produced by using the metallocene catalyst can even further suppress the odor generated from the stretchable film of the present invention.

Examples of the non-elastomeric olefin-based resin include an α-olefin homopolymer, a copolymer of two or more kinds of α-olefins, block polypropylene, random polypropylene, and a copolymer of one or two or more kinds of α-olefins and any other vinyl monomer. A copolymerization form in any such copolymer is, for example, a block form or a random form.

Examples of the α-olefin include α-olefins each having 2 to 12 carbon atoms. Examples of such α-olefin include ethylene, propylene, 1-butene, and 4-methyl-1-pentene.

Examples of the α-olefin homopolymer include polyethylene (PE), homopolypropylene (PP), poly(1-butene), and poly(4-methyl-1-pentene).

Examples of the polyethylene (PE) include low-density polyethylene (LDPE), linear low-density polyethylene (LLDPE), medium-density polyethylene (MDPE), and high-density polyethylene (HDPE).

The structure of the homopolypropylene (PP) may be any one of isotactic, atactic, and syndiotactic structures.

The non-elastomeric olefin-based resin preferably contains at least one kind selected from polyethylene (PE) and homopolypropylene (PP), and more preferably contains at least one kind selected from high-density polyethylene (HDPE), low-density polyethylene (LDPE), linear low-density polyethylene (LLDPE), and homopolypropylene (PP) because the effects of the present invention can be expressed to a larger extent. When the non-elastomeric olefin-based resin contains at least one kind selected from the high-density polyethylene (HDPE), the low-density polyethylene (LDPE), the linear low-density polyethylene (LLDPE), and the homopolypropylene (PP), a stretchable film even more excellent in handleability can be provided. The content of at least one kind selected from the high-density polyethylene (HDPE), low-density polyethylene (LDPE), the linear low-density polyethylene (LLDPE), and the homopolypropylene (PP) in the non-elastomeric olefin-based resin is preferably from 50 wt % to 100 wt %, more preferably from 70 wt % to 100 wt %, still more preferably from 80 wt % to 100 wt %, still further more preferably from 90 wt % to 100 wt %, particularly preferably from 95 wt % to 100 wt %, most preferably substantially 100 wt % because the effects of the present invention can be expressed to a larger extent.

Examples of the copolymer of two or more kinds of α-olefins include an ethylene/propylene copolymer, an ethylene/1-butene copolymer, an ethylene/propylene/1-butene copolymer, a copolymer of ethylene/α-olefin having 5 to 12 carbon atoms, and a copolymer of propylene/α-olefin having 5 to 12 carbon atoms.

Examples of the copolymer of one or two or more kinds of α-olefins and any other vinyl monomer include an ethylene/vinyl acetate copolymer, an ethylene/acrylic acid alkyl ester copolymer, an ethylene/methacrylic acid alkyl ester copolymer, and an ethylene-non-conjugated diene copolymer.

A commercial product may be used as the non-elastomeric olefin-based resin.

The stretchable film of the present invention includes the filler. The filler is preferably at least one kind selected from inorganic particles and organic particles. The filler may be only one kind of filler, or may be two or more kinds of fillers. When the stretchable film of the present invention contains the filler, the stretchable film of the present invention can express excellent air permeability.

Examples of the inorganic particles include talc, titanium oxide, calcium oxide, magnesium oxide, zinc oxide, calcium carbonate, silica, clay, mica, barium sulfate, whisker, and magnesium hydroxide.

Examples of the organic particles include acrylic beads, styrene beads, and silicone resin particles.

Any appropriate average particle diameter may be adopted as the average particle diameter of the filler to the extent that the effects of the present invention are not impaired. A lower limit for such average particle diameter of the filler is preferably 0.5 μm or more, more preferably 0.6 μm or more, still more preferably 0.7 μm or more, and an upper limit therefor is preferably 50 μm or less, more preferably 30 μm or less, still more preferably 10 μm or less, particularly preferably 5 μm or less. The adjustment of the average particle diameter of the filler within the range enables the stretchable film of the present invention to express more excellent air permeability.

Any appropriate content may be adopted as the content of the filler to the extent that the effects of the present invention are not impaired. A lower limit for such content of the filler is preferably 50 parts by weight or more, more preferably 70 parts by weight or more, still more preferably 100 parts by weight or more, and an upper limit therefor is preferably 400 parts by weight or less, more preferably 350 parts by weight or less, still more preferably 300 parts by weight or less, with respect to 100 parts by weight of the olefin-based resin in the stretchable film. The adjustment of the content of the filler within the range enables the stretchable film of the present invention to express more excellent air permeability.

The filler may be coated with a releasing agent for preventing aggregation. Examples of such releasing agent include a fatty acid amide-based releasing agent, a silicone-based releasing agent, a fluorine-based releasing agent, and a long-chain alkyl-based releasing agent. Of those, a fatty acid amide-based releasing agent is preferred, and a saturated fatty acid bisamide is more preferred. Any appropriate usage amount may be adopted as the usage amount of the releasing agent.

The stretchable film of the present invention may contain any appropriate other component to the extent that the effects of the present invention are not impaired. The other component may be only one kind of component, or may be two or more kinds of components. Examples of such other component include a UV absorber, a heat stabilizer, a releasing agent, a lubricant, a colorant (e.g., a dye), an antioxidant, an anti-build up agent, an antiblocking agent, a foaming agent, other polymers, a tackifier, a plasticizer, an antidegradant, an antistatic agent, and a light stabilizer. Those components may be used alone or in combination thereof.

Examples of the UV absorber include a benzotriazole-based compound, a benzophenone-based compound, and a benzoate-based compound. Any appropriate content may be adopted as the content of the UV absorber as long as the UV absorber does not bleed out at the time of the forming.

Examples of the heat stabilizer include a hindered amine-based compound, a phosphorus-based compound, and a cyanoacrylate-based compound. Any appropriate content may be adopted as the content of the heat stabilizer as long as the heat stabilizer does not bleed out at the time of the forming.

Examples of the releasing agent include a fatty acid amide-based releasing agent, a silicone-based releasing agent, a fluorine-based releasing agent, and a long-chain alkyl-based releasing agent. Of those, a fatty acid amide-based releasing agent is preferred from the viewpoint that a peeling layer more excellent in balance between peelability and resistance against contamination due to bleedout can be formed, and a saturated fatty acid bisamide is more preferred. Any appropriate content may be adopted as the content of the releasing agent.

The stretchable film of the present invention is preferably obtained by subjecting an unstretched film to a stretching treatment. Such stretching treatment of the unstretched film may be referred to as "pre-extension". When the unstretched film is subjected to the stretching treatment, the stretchable film of the present invention can express more excellent stretchability. In addition, when the unstretched film is subjected to the stretching treatment, the stretchable film of the present invention can even further express excellent air permeability by being combined with the filler.

The pre-extension is pre-extension having the following meaning: the stretchable film of the present invention is extended in advance in consideration of the fact that the stretchable film is extended again (post-extension) in its final use (e.g., at the time of the production of a diaper and at the time of the use of the diaper).

The pre-extension is preferably performed after the stretchable film of the present invention has been produced and sufficiently solidified.

The pre-extension may be performed on the entirety of the original length or width in at least one direction, or may be performed on part of the original length or width. In addition, the pre-extension may be performed in any appropriate direction. The pre-extension is preferably performed on the original length or width in at least one direction.

The extension degree of the pre-extension is preferably 1.5 times or more and less than 2.5 times (typically 2.0 times), more preferably 2.5 times or more and less than 3.5 times (typically 3.0 times), still more preferably 3.5 times or more and less than 4.5 times (typically 4.0 times), particularly preferably 4.5 times or more and less than 5.5 times (typically 5.0 times). For example, 2.0-time pre-extension means that when the original length of the stretchable film is represented by L, the stretchable film is extended (sometimes referred to as "stretched") to have a length of 2 L. The stretchable film of the present invention can express more excellent stretchability by being pre-extended to such extension degree. In addition, when the stretchable film of the present invention is pre-extended to such extension degree, the stretchable film can even further express excellent air permeability by being combined with the filler.

The pre-extension is preferably performed at a temperature less than the melting point of the olefin-based resin. The stretchable film of the present invention can express more excellent stretchability by being pre-extended at such temperature. In addition, when the stretchable film of the present invention is pre-extended at such temperature, the stretchable film can even further express excellent air permeability by being combined with the filler.

When the stretchable film of the present invention is preferably pre-extended as described above, the olefin-based resin undergoes plastic deformation or is extended beyond the brittle fracture point of the olefin-based resin, and hence the film can express excellent stretchability.

《Production of Stretchable Film》

Any appropriate method may be adopted as a method of producing the stretchable film of the present invention to the extent that the effects of the present invention are not impaired. The stretchable film is preferably obtained by: producing an unstretched film by any appropriate method; and then subjecting the unstretched film to a stretching treatment. The stretching treatment is preferably performed after the unstretched film has been produced and sufficiently solidified. Details about the stretching treatment are as described in the foregoing.

A method of producing the unstretched film is typically, for example, a method involving molding materials for the stretchable film of the present invention with a T-die molding machine to produce the unstretched film. For example, a rolled body of the stretchable film of the present invention can be produced by: extruding the materials for the stretchable film with the T-die molding machine from its T-die; and then winding the extruded materials in a roll shape. In addition to the T-die method involving using the T-die, an inflation method or the like can also be adopted.

《Application of Stretchable Film》

The stretchable film of the present invention can be used in any appropriate article in which the effects of the present invention can be effectively utilized. That is, the article of the present invention includes the stretchable film of the present invention. A typical example of such article is a sanitary article. Examples of such sanitary article include a diaper (in particular, such a diaper that the stretchable film of the present invention is used as a stretchable material in an ear portion or a stretchable material in the opening portion of waist surroundings or leg surroundings (a waist band or a gather)), a supporter, and a mask.

EXAMPLES

The present invention is hereinafter specifically described by way of Examples. However, the present invention is by no means limited to these Examples. Test and evaluation methods in Examples and the like are as described below. In addition, "part(s)" means "part(s) by weight" and "%" means "wt %" unless otherwise stated.

<Method of Evaluating Air Permeability>

Air permeability was measured with an Oken-type air permeability meter (sec/100 cc) (manufactured by Asahi Seiko Co., Ltd., product name: EG01-7-7MR). A stretchable film having an air permeability of more than 99,999 sec/100 cc was judged to have "no air permeability." In Table 1, the column "Film as it is" means that the air permeability of a produced film was measured while the film was kept as it was. In addition, in Table 1, the column "Twice in transverse direction" means that the air permeability of a produced film was measured under a state in which the film was extended twice in its transverse direction.

Example 1

70 Parts by weight of amorphous PP (manufactured by Exxon Mobil Corporation, product name: Vistamaxx 6202), 30 parts by weight of an ethylene-based elastomer (manufactured by Mitsui Chemicals, Inc., Tafmer PN-2070), and 150 parts by weight of calcium carbonate were loaded into an extruder, and were extruded from its T-die to produce an unstretched film (1) having a thickness of 150 µm.

Next, the unstretched film (1) was pre-stretched in its machine direction at a ratio of 3.8 times to provide a stretchable film (1).

The results are shown in Table 1.

Example 2

70 Parts by weight of amorphous PP (manufactured by Exxon Mobil Corporation, product name: Vistamaxx 6202), 30 parts by weight of an ethylene-based elastomer (manufactured by Mitsui Chemicals, Inc., Tafmer PN-2070), and 250 parts by weight of calcium carbonate were loaded into an extruder, and were extruded from its T-die to produce an unstretched film (2) having a thickness of 150 µm.

Next, the unstretched film (2) was pre-stretched in its machine direction at a ratio of 3.8 times to provide a stretchable film (2).

The results are shown in Table 1.

Example 3

100 Parts by weight of polyethylene (HDPE) (manufactured by Tosoh Corporation, product name: Nipolon Hard 1000) and 150 parts by weight of calcium carbonate (average particle diameter=1.1 μm) were loaded into a surface layer extruder. 100 Parts by weight of amorphous PP (manufactured by Exxon Mobil Corporation, product name: Vistamaxx 7010) and 150 parts by weight of calcium carbonate (average particle diameter=1.1 μm) were loaded into an intermediate layer extruder. The materials were co-extruded in three layers from the T-dies of the extruders to produce an unstretched film (3) having a thickness of 80 μm.

Next, the unstretched film (3) was pre-stretched in its transverse direction at a ratio of 3.8 times to provide a stretchable film (3).

The results are shown in Table 2.

Example 4

30 Parts by weight of amorphous PP (manufactured by Exxon Mobil Corporation, product name: Vistamaxx 7010), 70 parts by weight of polyethylene (LLDPE) (manufactured by Prime Polymer Co., Ltd., product name: ULTZEX 2022L), and 150 parts by weight of calcium carbonate (average particle diameter=1.1 μm) were loaded into a surface layer extruder. 100 Parts by weight of amorphous PP (manufactured by Exxon Mobil Corporation, product name: Vistamaxx 7010) and 150 parts by weight of calcium carbonate (average particle diameter=1.1 μm) were loaded into an intermediate layer extruder. The materials were co-extruded in three layers from the T-dies of the extruders to produce an unstretched film (3) having a thickness of 80 μm.

Next, the unstretched film (3) was pre-stretched in its transverse direction at a ratio of 3.8 times to provide a stretchable film (3).

The results are shown in Table 2.

TABLE 1

| | Formulation | | Air permeability (sec/100 cc) | |
| --- | --- | --- | --- | --- |
| | Olefin-based resin | Filler | Film as it is | Twice in transverse direction |
| Example 1 | Vistamaxx 6202 (70 parts by weight) | Tafmer PN-2070 (30 parts by weight) | Calcium carbonate (150 parts by weight) | 72,533 | 1,037 |
| Example 2 | Vistamaxx 6202 (70 parts by weight) | Tafmer PN-2070 (30 parts by weight) | Calcium carbonate (250 parts by weight) | 653 | 280 |

TABLE 2

| | | Formulation | | | Air permeability (sec/100 cc) | |
| --- | --- | --- | --- | --- | --- | --- |
| | | Olefin-based resin | | Filler | Film as it is | Twice in transverse direction |
| Example 3 | Surface layer (10%) | Nipolon Hard 1000 (100 parts by weight) | | Calcium carbonate (150 parts by weight) | 14,175 | 429 |
| | Intermediate layer (80%) | Vistamaxx 7010 (100 parts by weight) | | Calcium carbonate (150 parts by weight) | | |
| | Surface layer (10%) | Nipolon Hard 1000 (100 parts by weight) | | Calcium carbonate (150 parts by weight) | | |
| Example 4 | Surface layer (10%) | Vistamaxx 7010 (30 parts by weight) | ULTZEX 2022L (70 parts by weight) | Calcium carbonate (150 parts by weight) | 84,465 | 1,211 |
| | Intermediate layer (80%) | Vistamaxx 7010 (100 parts by weight) | | Calcium carbonate (150 parts by weight) | | |
| | Surface layer (10%) | Vistamaxx 7010 (30 parts by weight) | ULTZEX 2022L (70 parts by weight) | Calcium carbonate (150 parts by weight) | | |

INDUSTRIAL APPLICABILITY

The stretchable film of the present invention can be used in any appropriate article in which the effects of the present invention can be effectively utilized. That is, the article of the present invention includes the stretchable film of the present invention. A typical example of such article is a sanitary article. Examples of such sanitary article include a diaper (in particular, such a diaper that the stretchable film of the present invention is used as a stretchable material in an ear portion or a stretchable material in the opening portion of waist surroundings or leg surroundings (a waist band or a gather)), a supporter, and a mask.

REFERENCE SIGNS LIST

10 Olefin-based resin
20 Filler
30 Void
100 Stretchable film

The invention claimed is:

1. A stretchable film, comprising:
an olefin-based resin which is an olefin-based elastomer, a non-elastomeric olefin-based resin, or a blend of an olefin-based elastomer, and a non-elastomeric olefin-based resin; and
a filler,
wherein the stretchable film is formed of a laminate of three layers, the laminate having a layer construction of "layer A/layer B/layer C",
wherein each of layer A, layer B, and layer C comprises the olefin-based elastomer and each of layer A and layer C comprises the non-elastomeric olefin-based resin,
wherein the olefin-based elastomer of the layer B comprises an amorphous polypropylene and the layer B is free of a any non-elastomeric olefin-based resin,
wherein the content of the olefin-based elastomer in the olefin-based resin is from 20 wt. % to 30 wt. % in each of layer A and layer C,
wherein the content of the non-elastomeric olefin-based resin in the olefin-based resin is from 70 wt. % to 80 wt. % in each of layer A and layer C,
wherein the content of the filler in each of layer A, layer B, and layer C is 50 parts by weight or more with respect to 100 parts by weight of the olefin-based resin in each of layer A, layer B, and layer C in the stretchable film,
wherein stretching of the stretchable film produces voids in a surface thereof,
wherein the stretchable film is obtained by subjecting an unstretched film to a stretching treatment, wherein the unstretched film is stretched in at least one direction to a degree of 3.5 times or more and less than 4.5 times, and
wherein the air permeability is 429 sec/100 cc to 1211 sec/100 cc when extended twice in its transverse direction.

2. The stretchable film according to claim 1, wherein the stretchable film is used in a sanitary article.

3. An article, comprising the stretchable film of claim 1.

4. The stretchable film according to claim 1, wherein the olefin-based elastomer has a density of from 0.890 g/cm³ to 0.830 g/cm³.

5. The stretchable film according to claim 1, wherein the thickness of each of the A layer A and the C layer C serving as surface layers is from 2 μm to 40 μm, and the thickness of the B layer B serving as an intermediate layer is from 10 μm to 70 μm.

6. The stretchable film according to claim 5, wherein the thickness of each of the A layer A and the C layer C serving as surface layers is from 2 μm to 8 μm, and the thickness of the B layer B serving as an intermediate layer is from 40 μm to 70 μm.

7. The stretchable film according to claim 1, wherein the olefin-based elastomer has an MFR at 230° C. and 2.16 kgf of from 1.0 g/10 min to 25.0 g/10 min.

8. The stretchable film according to claim 1, wherein
the olefin-based elastomer of each of layer A and layer C is an olefin block copolymer, an olefin random copolymer, an ethylene copolymer, a propylene copolymer, an ethylene olefin block copolymer, a propylene olefin block copolymer, an ethylene olefin random copolymer, a propylene olefin random copolymer, an ethylene propylene random copolymer, an ethylene (1-butene) random copolymer, an ethylene (1-pentene) olefin block copolymer, an ethylene (1-hexene) random copolymer, an ethylene (1-heptene) olefin block copolymer, an ethylene (1-octene) olefin block copolymer, an ethylene (1-nonene) olefin block copolymer, an ethylene (1-decene) olefin block copolymer, a propylene ethylene olefin block copolymer, an ethylene (α-olefin) copolymer, an ethylene (α-olefin) random copolymer, an ethylene (α-olefin) block copolymer, amorphous polypropylene, combinations of the above-mentioned polymers and polyethylene, combinations of the above-mentioned polymers and polypropylene, or combinations thereof, and
the non-elastomeric olefin-based resin is an α-olefin homopolymer, a copolymer of two or more α-olefins, block polypropylene, random polypropylene, or a copolymer of at least one α-olefin and any other vinyl monomer.

9. The stretchable film according to claim 1, wherein the olefin-based elastomer of each of layer A and layer C is an ethylene-based elastomer, a propylene-based elastomer, or a 1-butene-based elastomer, and
the non-elastomeric olefin-based resin comprises at least one of high-density polyethylene (HDPE), low-density polyethylene (LDPE), linear low-density polyethylene (LLDPE), and homopolypropylene (PP).

10. The stretchable film according to claim 1, wherein the average particle diameter of the filler is 0.7 μm to 5 μm.

11. The stretchable film according to claim 1, wherein the olefin-based resin of the B layer B consists of amorphous polypropylene, and the olefin-based resin of each of layers A and C is amorphous polypropylene and non-elastomeric linear low density polyethylene (LLDPE).

12. The stretchable film according to claim 1 wherein the olefin-based elastomer of each of layer A, layer B, and layer C is the same, and the non-elastomeric olefin-based resin in layer A and layer C is the same.

13. A stretchable film, comprising:
an olefin-based resin; and
a filler,
wherein the stretchable film is formed of a laminate of three layers wherein each layer comprises the filler, the laminate having a layer construction of "layer A/layer B/layer C",
wherein the olefin-based resin of each of layer A and layer C comprises non-elastomeric high density polyethylene (HDPE), wherein the olefin-based resin of the layer B consists of amorphous polypropylene, wherein the stretchable film is obtained by subjecting an unstretched film to a stretching treatment, wherein the unstretched film is stretched in at least one direction to a degree of 3.5 times or more and less than 4.5 times, and wherein the air permeability is 429 sec/100 cc to 1211 sec/100 cc when extended twice in its transverse direction.

14. The stretchable film according to claim 13, wherein the content of the filler in each of layer A, layer B, and layer C is 50 parts by weight or more with respect to 100 parts by weight of the olefin-based resin of each of layer A, layer B, and layer C in the stretchable film.

15. The stretchable film according to claim 13, wherein the olefin-based resin of each of layers A and C is non-elastomeric high density polyethylene (HDPE).

* * * * *

UNITED STATES PATENT AND TRADEMARK OFFICE
CERTIFICATE OF CORRECTION

| | |
|---|---|
| PATENT NO. | : 11,305,034 B2 |
| APPLICATION NO. | : 15/564302 |
| DATED | : April 19, 2022 |
| INVENTOR(S) | : Kohei Takeda et al. |

It is certified that error appears in the above-identified patent and that said Letters Patent is hereby corrected as shown below:

In the Claims

At Column 15, Line 37 (Claim 1, Line 15) please change "of a any" to -- of any --;

At Column 15, Line 67 (Claim 5, Line 2) please change "the A layer A and the C layer C" to -- the layer A and the layer C --;

At Column 16, Line 2 (Claim 5, Line 4) please change "the B layer B" to -- the layer B --;

At Column 16, Line 5 (Claim 6, Line 2) please change "the A layer A and the C layer C" to -- the layer A and the layer C --;

At Column 16, Line 7 (Claim 6, Line 4) please change "the B layer B" to -- the layer B --; and At Column 16, Line 50 (Claim 11, Line 2) please change "the B layer B" to -- the layer B --.

Signed and Sealed this
Twenty-third Day of August, 2022

Katherine Kelly Vidal
*Director of the United States Patent and Trademark Office*